United States Patent [19]

Axen et al.

[11] 4,328,338

[45] May 4, 1982

[54] 2,5-INTER-O-PHENYLENE-3,4-DINOR-6,9α-EPOXY-6β-PGF₁ AMIDES

[75] Inventors: Udo F. Axen, Plainwell; John C. Sih, Kalamazoo, both of Mich.

[73] Assignee: The Upjohn Company, Kalamazoo, Mich.

[21] Appl. No.: 165,838

[22] Filed: Jul. 3, 1980

Related U.S. Application Data

[60] Division of Ser. No. 62,443, Jul. 31, 1979, Pat. No. 4,312,810, which is a continuation-in-part of Ser. No. 962,845, Nov. 22, 1978, abandoned.

[51] Int. Cl.³ .......................................... C07D 307/935
[52] U.S. Cl. .................................... 542/426; 542/429; 544/153; 544/373; 546/196; 546/265; 546/269; 260/330.9; 548/525; 549/465

[58] Field of Search ..................... 260/346.73, 326.34; 542/426, 429; 544/153, 373; 546/196, 265, 269

[56] References Cited

U.S. PATENT DOCUMENTS 4,175,202  11/1979  Nelson ............................... 562/463

*Primary Examiner*—Henry R. Jiles
*Assistant Examiner*—Bernard Dentz
*Attorney, Agent, or Firm*—Robert A. Armitage

[57] ABSTRACT

The present invention provides 2,5-inter-o-phenylene-3,4-dinor-6,9α-epoxy-6β-PGF₁ amides. These compounds are useful for a wide variety of pharmacological and therapeutical purposes, e.g., as antithrombotic agents.

1 Claim, No Drawings

2,5-INTER-O-PHENYLENE-3,4-DINOR-6,9α-EPOXY-6β-PGF₁ AMIDES

CROSS REFERENCE TO RELATED APPLICATION

This application is a division of Ser. No. 62,443, filed July 31, 1979, now U.S. Pat. No. 4,312,810, which is a continuation-in-part of Ser. No. 962,845, filed Nov. 22, 1978, now abandoned.

BACKGROUND OF THE INVENTION

The present invention relates to novel prostacyclin analogs and intermediates for their production. Most particularly, the present invention provides 2,5-inter-o-phenylene-3,4-dinor-6,9α-epoxy-6β-PGF₁ amides. The preparation and use of the novel compounds described herein is incorporated here by reference from U.S. Pat. No. 4,281,113.

SUMMARY OF THE INVENTION

The present invention particularly provides a prostacyclin analog of formula VI

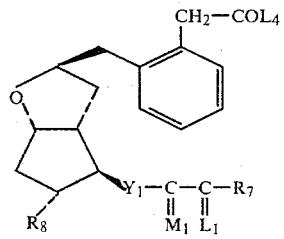

wherein $R_8$ is hydrogen, hydroxy, or hydroxymethyl;
wherein $Y_1$ is
(1) trans—CH=CH—,
(2) cis—CH=CH—,
(3) —CH$_2$CH$_2$, or
(4) —C≡C—,
wherein $M_1$ is $\alpha$-$R_5$:$\beta$-OH or $\alpha$-OH:$\beta$-$R_5$, wherein $R_5$ is hydrogen or alkyl with one to 4 carbon atoms, inclusive,
wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\alpha$-$R_4$:$\beta$-$R_3$, wherein $R_3$ and $R_4$ are hydrogen, methyl, or fluoro, being the same or different, with the proviso that one of $R_3$ and $R_4$ is fluoro only when the other is hydrogen or fluoro;
wherein $R_7$ is
(1) —(CH$_2$)$_m$—CH$_3$, wherein m is an integer from one to 5, inclusive;
(2) phenoxy;
(3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;
wherein $L_4$ is
(1) amino of the formula —NR$_{21}$R$_{22}$, wherein $R_{21}$ and $R_{22}$ are
  (a) hydrogen;
  (b) alkyl of one to 12 carbon atoms, inclusive;
  (c) cycloalkyl of 3 to 10 carbon atoms, inclusive;
  (d) aralkyl of 7 to 12 atoms, inclusive;
  (e) phenyl;
  (f) phenyl substituted with one, 2 or 3 chloro, alkyl of one to 3 carbon atoms, inclusive, hydroxy, carboxy, alkoxycarbonyl of one to 4 carbon atoms, inclusive, or nitro;
  (g) carboxyalkyl of 2 to 5 carbon atoms, inclusive;
  (h) carbamoylalkyl of 2 to 5 carbon atoms, inclusive;
  (i) cyanoalkyl of 2 to 5 carbon atoms, inclusive;
  (j) acetylalkyl of 3 to 6 carbon atoms, inclusive;
  (k) benzoylalkyl of 7 to 11 carbon atoms, inclusive;
  (l) benzoylalkyl substituted by one, 2 or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
  (m) pyridyl;
  (n) pyridyl substituted by one, 2 or 3 chloro, alkyl of one to 3 carbon atoms, inclusive, or alkoxy of one to 3 carbon atoms, inclusive;
  (o) pyridylalkyl of 6 to 9 carbon atoms, inclusive;
  (p) pyridylalkyl substituted by one, 2 or 3 chloro, alkyl of one to 3 carbon atoms, inclusive, hydroxy or alkoxy of one to 3 carbon atoms, inclusive;
  (q) hydroxyalkyl of one to 4 carbon atoms, inclusive;
  (r) dihydroxyalkyl of one to 4 carbon atoms; or
  (s) trihydroxyalkyl of one to 4 carbon atoms; with the further proviso that not more than one of $R_{21}$ and $R_{22}$ is other than hydrogen or alkyl;
(2) cycloamino selected from the group consisting of
  (a) pyrrolidino,
  (b) piperidino,
  (c) morpholino,
  (d) piperazino,
  (e) hexamethyleneimino,
  (f) pyrrolino,
  (g) 3,4-didehydropiperidinyl, or
  (h) pyrrolidino, piperidino, morpholino, piperazino, hexamethyleneimino, pyrrolino, or 3,4-didehydropiperidinyl substituted by one or 2 alkyl of one to 12 carbon atoms, inclusive;
(3) carbonylamino of the formula —NR$_{23}$COR$_{21}$, wherein $R_{23}$ is hydrogen or alkyl of one to 4 carbon atoms, inclusive, and $R_{21}$ is other than hydrogen, but otherwise as defined above; or
(4) sulfonylamino of the formula —NR$_{23}$SO$_2$R$_{21}$, wherein $R_{21}$ and $R_{23}$ are as defined in (3).

The novel prostaglandin analogs are useful for a variety of prostacyclin-like pharmacological purposes, particularly and especially as inhibitors of platelet aggregation in vivo and in vitro. Thus, these prostacyclin analogs are useful for a variety of pharmacological and therapeutic purposes, e.g., as antithrombotic agents.

We claim:

1. A prostacyclin analog of formula VI

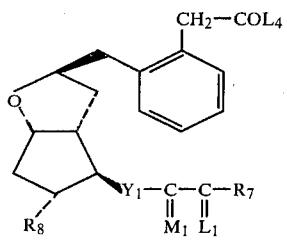

wherein $R_8$ is hydrogen, hydroxy, or hydroxymethyl;
wherein $Y_1$ is
- (1) trans—CH=CH—,
- (2) cis—CH=CH—,
- (3) —CH$_2$CH$_2$, or
- (4) —C≡C—, wherein $M_1$ is $\alpha$-$R_5$:$\beta$-OH or $\alpha$-OH:$\beta R_5$, wherein $R_5$ is hydrogen or alkyl with one to 4 carbon atoms, inclusive, wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\alpha$-$R_4$:$\beta$-$R_3$, wherein $R_3$ and $R_4$ are hydrogen, methyl, or fluoro, being the same or different, with the proviso that one of $R_3$ and $R_4$ is fluoro only when the other is hydrogen or fluoro;

wherein $R_7$ is
- (1) —(CH$_2$)$_m$—CH$_3$, wherein m is an integer from one to 5, inclusive;
- (2) phenoxy;
- (3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
- (4) phenyl;
- (5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
- (6) phenylmethyl, phenylethyl, or phenylpropyl; or
- (7) phenylmethyl, phenylethyl, or phenylpropyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;

wherein $L_4$ is
- (1) amino of the formula —NR$_{21}$R$_{22}$, wherein $R_{21}$ and $R_{22}$ are
  - (a) hydrogen;
  - (b) alkyl of one to 12 carbon atoms, inclusive;
  - (c) cycloalkyl of 3 to 10 carbon atoms, inclusive;
  - (d) aralkyl of 7 to 12 carbon atoms, inclusive;
  - (e) phenyl;
  - (f) phenyl substituted with one, 2 or 3 chloro, alkyl of one to 3 carbon atoms, inclusive, hydroxy, carboxy, alkoxycarbonyl of one to 4 carbn atoms, inclusive, or nitro;
  - (g) carboxyalkyl of 2 to 5 carbon atoms, inclusive;
  - (h) carbamoylalkyl of 2 to 5 carbon atoms, inclusive;
  - (i) cyanoalkyl of 2 to 5 carbon atoms, inclusive;
  - (j) acetylalkyl of 3 to 6 carbon atoms, inclusive;
  - (k) benzoylalkyl of 7 to 11 carbon atoms, inclusive;
  - (l) benzoylalkyl substituted by one, 2 or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
  - (m) pyridyl;
  - (n) pyridyl substituted by one, 2 or 3 chloro, alkyl of one to 3 carbon atoms, inclusive, or alkoxy of one to 3 carbon atoms, inclusive;
  - (o) pyridylalkyl of 6 to 9 carbon atoms, inclusive;
  - (p) pyridylalkyl substituted by one, 2 or 3 chloro, alkyl of one to 3 carbon atoms, inclusive, hydroxy or alkoxy of one to 3 carbon atoms, inclusive;
  - (q) hydroxyalkyl of one to 4 carbon atoms, inclusive;
  - (r) dihydroxyalkyl of one to 4 carbon atoms; or
  - (s) trihydroxyalkyl of one to 4 carbon atoms;
  with the further proviso that not more than one of $R_{21}$ and $R_{22}$ is other than hydrogen or alkyl;
- (2) cycloamino selected from the group consisting of
  - (a) pyrrolidino,
  - (b) piperidino,
  - (c) morpholino,
  - (d) piperazino,
  - (e) hexamethyleneimino,
  - (f) pyrrolino,
  - (g) 3,4-didehydropiperidinyl, or
  - (h) pyrrolidino, piperidino, morpholino, piperazino, hexamethyleneimino, pyrrolino, or 3,4-didehydropiperidinyl substituted by one or 2 alkyl of one to 12 carbon atoms, inclusive;
- (3) carbonylamino of the formula —NR$_{23}$COR$_{21}$, wherein $R_{23}$ is hydrogen or alkyl of one to 4 carbon atoms, inclusive, and $R_{21}$ is other than hydrogen, but otherwise as defined above; or
- (4) sulfonylamino of the formula —NR$_{23}$SO$_2$R$_{21}$, wherein $R_{21}$ and $R_{23}$ are as defined in (3).

* * * * *